United States Patent [19]

Relander

[11] Patent Number: 5,833,977
[45] Date of Patent: Nov. 10, 1998

[54] METHOD OF IMPROVING THE QUALITY OF PLANT SEEDS USING LACTIC ACID PRODUCING MICRO-ORGANISMS

[75] Inventor: Harald Relander, Lahti, Finland

[73] Assignee: Oy Lahden Polttimo AB, Lahiti, Finland

[21] Appl. No.: 765,931

[22] PCT Filed: Jul. 5, 1995

[86] PCT No.: PCT/FI95/00391

§ 371 Date: Jan. 14, 1997

§ 102(e) Date: Jan. 14, 1997

[87] PCT Pub. No.: WO96/02141

PCT Pub. Date: Feb. 1, 1996

[30] Foreign Application Priority Data

Jul. 14, 1994 [FI] Finland ..................................... 943366

[51] Int. Cl.⁶ .......................... A01N 63/00; A01N 25/00; C12C 1/00; C12N 1/00
[52] U.S. Cl. .......................... 424/93.3; 424/405; 435/93; 435/243; 435/252.3
[58] Field of Search ................................... 435/252.3, 93, 435/243; 800/200; 424/93.3, 405

[56] References Cited

U.S. PATENT DOCUMENTS

| | | | |
|---|---|---|---|
| 4,725,436 | 2/1988 | Prillwitz et al. | 424/93 |
| 4,956,177 | 9/1990 | King et al. | 424/93 |
| 5,178,863 | 1/1993 | Toyoda et al. | 424/93 |
| 5,232,850 | 8/1993 | Casida, Jr. | 435/253.3 |
| 5,266,316 | 11/1993 | Elad et al. | 424/93 |
| 5,270,059 | 12/1993 | Janiswicz et al. | 424/935 |
| 5,288,633 | 2/1994 | Cartwright et al. | 435/253.3 |
| 5,294,442 | 3/1994 | Cotty | 424/93 |
| 5,314,691 | 5/1994 | Coffey et al. | 424/93 |

FOREIGN PATENT DOCUMENTS

| | | |
|---|---|---|
| 2 200 924 | 8/1988 | United Kingdom . |
| WO92/01038 | 1/1992 | WIPO . |
| WO92/18613 | 10/1992 | WIPO . |
| WO93/19602 | 10/1993 | WIPO . |
| WO94/16053 | 7/1994 | WIPO . |
| WO94/16053A1 | 7/1994 | WIPO . |
| WO94/19950 | 9/1994 | WIPO . |

OTHER PUBLICATIONS

Visser et al., "Antagonism of Lactic Acid Bacteria against Phytopathogenic Bacteria", Applied and Environmental Microbiology, Sep. 1986, vol. 52, No. 3, pp. 552–555.

Kvasnikov, E.I. et al. "Lactic Acid Bacteria and Methods of Their Use," Moscow, Nauka, 1975, pp. 225–229.

*Primary Examiner*—Nancy Degen
*Assistant Examiner*—Andrew Wang
*Attorney, Agent, or Firm*—McDermott, Will & Emery

[57] ABSTRACT

The invention relates to a method for improving the quality of the seeds of a plant by treating the plant, such as a cereal to be used in malting, with a lactic acid bacterial preparation. The treatment is performed in the field or under field conditions when the seeds develop by spraying the plant with the preparation. The invention also related to the use of the lactic acid bacterial preparation for spraying a plant in the field or under field conditions when its seeds develop. Furthermore, the invention relates to a plant product, such as a barley or rye product, which has been treated with the aforementioned method.

10 Claims, 1 Drawing Sheet

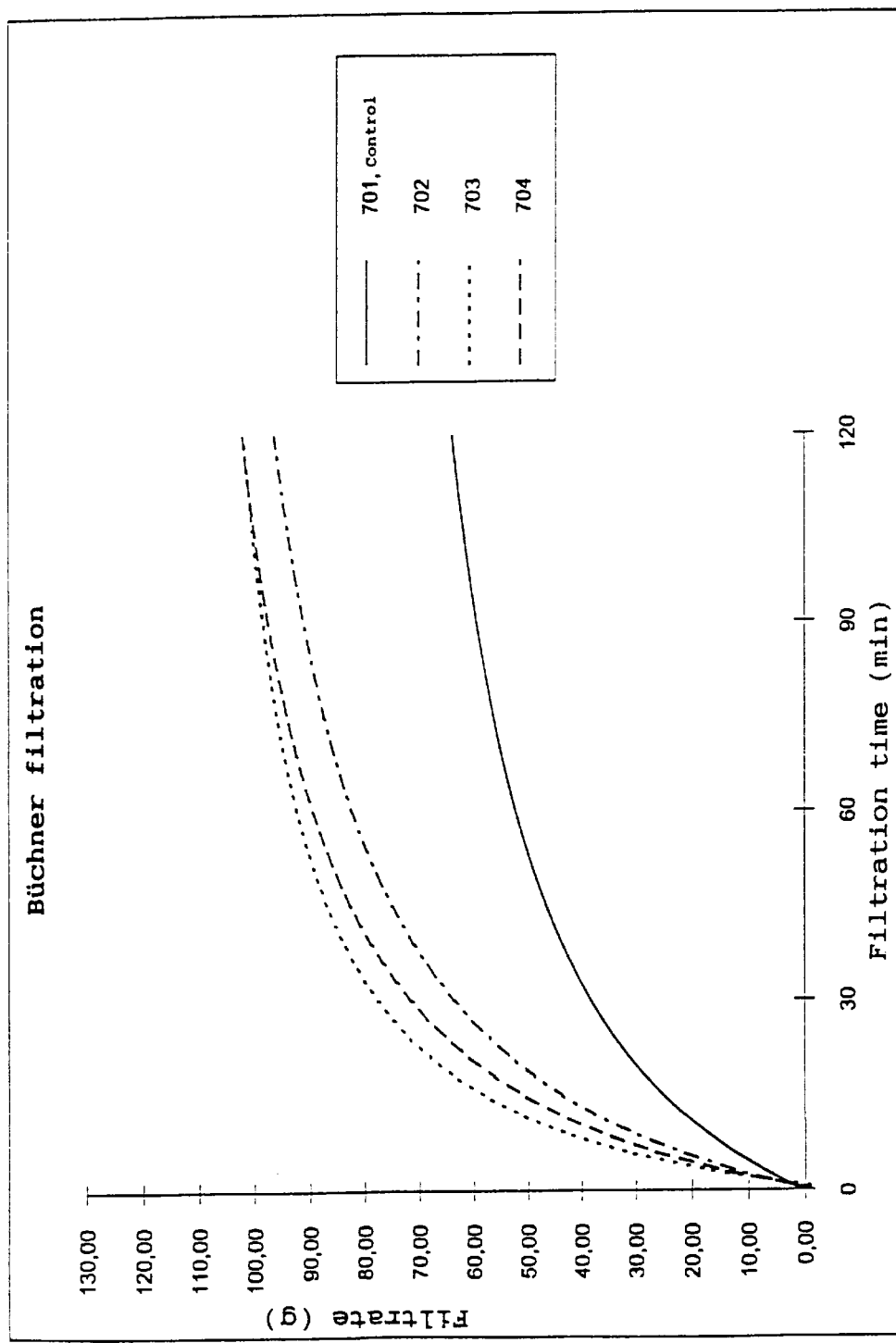
Figure 1. Effect of starter cultures on the filterability of wort prepared from the malt

METHOD OF IMPROVING THE QUALITY OF PLANT SEEDS USING LACTIC ACID PRODUCING MICRO-ORGANISMS

FIELD OF THE INVENTION

The present invention relates to a method of treating the seeds of plants. More precisely, the invention relates to a method wherein a plant, preferably a cereal, in particular a cereal, such as barley or rye, to be used in malting, is treated with a bacterial preparation affecting microbes in order to improve the quality of the seeds (kernels). The invention also relates to the use of a bacterial preparation for spraying a plant in the field or under field conditions as its seeds develop in order to improve the quality of the seeds. Furthermore, the invention relates to a plant product, e.g. a cereal product and in particular a barley or rye product, for example barley or rye malt, that has been treated with the aforementioned method.

BACKGROUND ART

Conventionally a cereal to be used in the manufacture of beer is malted so that the starch contained therein would convert to fermentable sugars. Unmalted cereal is also sometimes used in the manufacture of beer. The cereal most commonly used in malting is barley. It is well applicable in malting and in the manufacture of beer, since the husk of its kernel does not come off during threshing, but protects the kernel during malting. Broken kernels are susceptible to mould fungi. The good germinability of barley is important in malting, since kernels that have not germinated cannot be malted and are also susceptible to moulds. Malted barley is also used as a raw material for whisky.

Other cereals, such as wheat, rye and rice, can also be used in the preparation of malt.

The purpose of the malting is to provide physical, chemical and biochemical changes in the kernel, thus producing enzymes which in the so-called mashing stage during the manufacture of beer decompose the starch of the kernel into a form soluble in wort. Malting comprises several stages. Firstly, the cereal to be used is purified and screened, and it is then steeped in water to provide a suitable moisture content (ca. 45%). When the kernels are suitably moist, they are germinated usually about six days. After the germination the malt is dried and the moisture content thereby decreases to about 4%. After the kilning the rootlets are removed.

In a cereal, such as barley, used in malting, microbes originating in the field and possibly in the storing affect the development and activity of the microbial flora in the preparation of malt. Large amounts of microbes, especially high mould contents, may be harmful in the malting of a cereal. The mould content is one of the criteria of the quality of a cereal used in malting, and a maximum limit is often set for this content. Other factors influencing the quality of malt are the other quality characteristics of the cereal used as raw material, for example its protein content, the size distribution of the kernels, germination energy and water sensitivity. The type of the cereal, and the malting technique and conditions are also significant.

The natural microbial flora of barley comprises moulds such as Fusarium, Alternaria, Cephalosporium and Helminthosporium, and the genera of Rhizopus and Mucor. The occurrence of the moulds varies depending on the period of growth and the place of growth (soil). Wet and rainy weather during the ear emergence or harvesting of barley affects the growth of Fusarium moulds in particular. In malting the composition of the moulds varies considerably during germination, especially the amount of Fusarium moulds increases particularly during steeping. Rhizopus and Mucor in turn are prevalent in malts, since they multiply rapidly at temperatures occurring in the beginning of the drying.

The original bacterial and yeast flora of the cereal also affects the quality of the material to be malted. The natural enterobacteria, Pseudomonas species, lactic acid bacteria and yeasts of the cereal multiply during malting.

The microorganisms in the cereal and malt have both positive and negative effects. Many of the effects of the microbial flora are useful. The glucanolytic and proteolytic effects of moulds and bacteria are the ones most commonly reported. A lowered $\beta$-glucan content and extract difference describing malt modification, a reduced viscosity of the wort, an improved filterability of the wort, and an increased nitrogen content are the positive characteristics caused by the enzymatic activity of the microbes. The drawbacks of the microbial flora of a cereal and malt are the gushing of beer, possible mycotoxins, and the deterioration of germination.

The gushing of beer is caused by components originating in the moulds, especially of the genus Fusarium, contained in the material used for malting. In a cereal that is strongly contaminated by mould, an active mould mycelium forms peptides or peptide-containing compounds that survive the process for manufacturing beer and produce gushing. In order to avoid this extremely serious problem concerning the quality, the cereal samples used in the malting must be analyzed for mould contamination, and strongly contaminated batches must be discarded.

Controlling and preventing the gushing of beer is always very problematic. Adding microbicides in the steeping water decreases the growth of moulds, but the use of chemical preservatives is preferably avoided. Therefore it is of primary importance that the quality of the material to be malted is as good as possible. It is especially desirable to decrease the contamination of Fusarium moulds.

The water sensitivity of barley affects the germination. One possible reason for the water sensitivity of barley is that the dense microbial population on the surface of the kernels competes with the plant tissue for the oxygen to be used during the steeping. When a germ cannot obtain the oxygen it needs, the germination slows down or is completely prevented.

The lautering and filterability of the wort is primarily affected by the quality of the malt. The composition of the kernels used in turn determines the concentration of gelling proteins in the malt. The gelling proteins are partially degraded in malting, but they may aggregate in the preparation stage of the wort. The rate of filtration is affected by complexes formed between these proteins and pentosans, $\beta$-glucans, residual starch and lipids. In addition, the elevated amounts of bacteria may lead to problems in filtration. Good filterability is therefore one of the quality factors of malt. Improving the filterability also speeds up the brewing process.

Moulds are harmful contaminants not only in a cereal intended for use in the brewing industry, but also in a cereal and in other plants used as raw material for food and animal feed industries. Controlling the moulds is important in the storage of a cereal: changes in the temperature and the moisture content may cause a rapid increase in the mould population. For example in the animal feed industry, moulds like Fusarium may cause spoilage of the feed raw material or of the finished feed.

In order to prevent the growth of microbial flora, in particular Fusarium moulds, during malting, lactic acid bacteria have been used [Haikara, Mallas ja Olut 1 (1994) 5–15; Haikara et al., Eur. Brew. Conv. Proc. 24th Congr., Oslo 1993, 163–172]. Lactic acid bacteria in their culture medium, culture medium without cells, or cells separated from the culture medium were added to dried kernels of barley before the malting, to the steeping waters of the kernels, or in the beginning of the germination. The best result was obtained when the lactic acid bacteria were added in their culture medium two days before the malting. By means of the treatment it was possible to influence the properties of the malt, such as the filterability and viscosity of the wort obtained from the malt, and the amounts of microbes in the malt. The effect of the treatment on the gushing of beer was not tested. However, the treatment of barley kernels only after the harvesting and drying cannot prevent the damage caused by harmful microbes already in the field, for example the formation of gushing factors, a decrease of the falling number, and an increase in water sensitivity.

SUMMARY OF THE INVENTION

The present invention provides a novel method for decreasing or avoiding the above-described problems and drawbacks. It was unexpectedly found out that the quality of plant seeds can be improved when a plant is treated in the field or under field conditions during the development of the seeds with a lactic acid bacterial preparation which affects positively the quality characteristics of the seeds. This is especially surprising, since the treatment of a plant already when the seeds are developing in the field means interfering with very complex interaction between for example different members of the microbial flora, and between the microbial flora and the plant, whereupon the result was quite unexpected. Furthermore, the effect of external conditions, such as the weather and the conditions of growth, on the success of the treatment could not be predicted.

The present invention thus relates to a method of treating plants in order to improve the quality of the seeds by changing their microbial flora. The method is characterized in that the plant is treated in the field or under field conditions when the seeds develop by spraying it with a lactic acid bacterial preparation.

FIGURE

FIG. 1 graphically shows the effect of the lactic acid bacterial treatment according to the invention on the filtration of wort.

DETAILED DESCRIPTION OF THE INVENTION

According to the invention, it is possible to influence the quality of the seeds of a plant, preferably a cereal, by spraying it already in the field with a lactic acid bacterial preparation which changes the microbial flora and the quality characteristics of the seeds. The quality characteristics of a plant refer to all parameters measuring the quality of the plant, the most general parameters of e.g. a cereal being the protein content, the falling number, the size distribution of the kernels, germination energy, water sensitivity, total amount of microbes, and mould content, which in turn affect for example the baking properties of flour made of the cereal, or the results of an analysis of malt, wort and beer prepared from the cereal.

The present invention is preferably applicable in improving the quality of a cereal, such as barley, rye, wheat or rice, suitable for mill and baking industries and for malting. The cereal to be processed is preferably barley or rye, most preferably barley intended for malting.

The method according to the invention is particularly applicable in treating a cereal to be used for malting, whereupon the amount of mould decreases, especially contamination caused by Fusarium species, and the other quality characteristics of the material to be malted and of the finished malt are improved. The advantageous changes in the seeds of the cereal are apparent for example in an improved falling number measuring the baking properties, and in a lower water sensitivity as far as malting is concerned. In the finished malt the advantageous effects are evident in an increased extract yield, an improved malt modification, and a faster filterability or lautering performance of the wort. The method also decreases the gushing tendency of the beer made from the malt.

A growing plant is sprayed with a lactic acid bacterial preparation capable of improving the quality of the seeds by changing the total amount and/or internal proportions of the microbial flora in the seeds of the plant to be treated. Such a preparation can for example prevent or increase the growth of some microbes contained in the plant, whereupon changing the internal proportions and/or amounts of a microbial population brings about positive effects on the properties of the seeds of another microbial population.

The method according to the invention can utilize any lactic acid bacterial preparation which has the aforementioned properties and which does not reduce the useful properties of the microbes.

Lactic acid bacteria have been widely used as starter cultures in dairy, meat and plant industries and in the preservation of forage. Lactic acid bacteria produce organic acids which lower the pH of the fermentation, and some species of lactic acid bacteria also secrete bacteriocins or agents of low molecular weight, inhibiting the growth of microorganisms.

Lactic acid bacteria are advantageous also due to their safety. The use of lactic acid bacteria in the food industry is wide and accepted. Furthermore, the normal flora of a cereal comprises lactic acid bacteria.

The present invention can utilize any generally available lactic acid bacteria which have characteristics improving the quality of seeds. For example lactic acid bacteria naturally occurring in a cereal are suitable for this purpose. Useful lactic acid bacteria include the genera Lactobacillus, Pediococcus, Leuconostoc and Streptococcus. Lactic acid bacteria belonging to Lactobacillus and Pediococcus, and their mixtures are preferable. Lactic acid bacteria that are especially preferable in the method according to the invention include *Lactobacillus plantarum* and *Pediococcus pentosaceus*.

The invention also relates to the use of a lactic acid bacterial preparation for spraying a cereal in the field or under field conditions when its seeds are developing in order to improve the quality of the seeds. The treatment is suitably carried out during ear emergence for example when the cereal is about to ear up or is already earing. The invention further relates to a cereal product, especially a barley or rye product, for example barley or rye malt, which has been treated with the aforementioned method.

The lactic acid bacterial preparation to be sprayed on the field may be a bacterial culture, i.e. a culture medium containing the cells, as such or concentrated, a cell preparation comprising separated and possibly lyophilized cells suspended in water, in a culture medium or in some other suitable carrier, such as physiological saline, or a culture broth from which microbial cells have been removed, as such or concentrated. The lactic acid bacterial preparation preferably comprises living lactic acid bacteria.

The preparation to be sprayed on the fields preferably comprises a strain of *Lactobacillus plantarum* or *Pediococcus pentosaceus* in the culture broth as such or concentrated. The concentration may be performed in a conventional manner, for example through centrifugation, lyophilization, filtration or evaporation. A lyophilized lactic acid bacterial preparation, which in practical use is added to a suitable culture medium or diluting agent, is also advantageous for the easy implementation of the method.

The lactic acid bacterial preparation used in treating a cereal can be produced from a stock preparation according to conventional microbiological practice through subculturing and through gradual increasing of the volume until a suitable microbial density is obtained in the culture broth. A preparation useful in the present invention contains about $1 \times 10^8$ to $1 \times 10^{12}$ CFU/l, preferably about $1 \times 10^{10}$ to $1 \times 10^{12}$ CFU/l of lactic acid bacteria. In particular a preparation containing $1 \times 10^{10}$ to $1 \times 10^{11}$ CFU/l of lactic acid bacteria is used.

For the user, the most suitable preparation for spraying in the field might be a lyophilized preparation, which is mixed before the use with a suitable diluting agent, such as water, in an appropriate concentration, such as $1 \times 10^9$ to $1 \times 10^{11}$ CFU/l.

In the method according to the invention, the amount of the lactic acid bacterial preparation to be used in the spraying is calculated on the basis of a desired effective bacterial content that improves the quality of the seeds. For practical purpose, it is suitable to use an amount corresponding to 50 to 1000 l/ha, preferably 100 to 500 l/ha. A person skilled in the art can easily estimate the amount needed.

According to the present invention, a plant is treated when it grows in the field or under field conditions as the seeds develop. The expression "field conditions" refers here generally to the place of growth or cultivation of the plant to be treated. For example when a cereal is being treated, the spraying may be performed immediately after the beginning of the ear emergence or some time after this, for example 5 to 15 days later. For example the weather conditions affect the choice of the suitable time for spraying. In the examples below, the present invention will be described by means of its preferred embodiments without being restricted thereto, however.

EXAMPLE 1

Preparation of Lactic Acid Bacterial Cultures

Lactic acid bacterial cultures used in treating a cereal were prepared in the following manner. Strain VTT-E-78076 of *Lactobacillus plantarum*, isolated from beer, and strain VTT-E-90390 of *Pediococcus pentosaceus*, derived from broken kernels of barley, (from the culture collection of the Biotechnology and Food Research Section of the Technical Research Centre of Finland (VTT)) were aseptically inoculated from MRS agar (Oxoid) into 10 ml of MRS broth (Oxoid) where they were cultivated under anaerobic conditions at 30° C. for two days without mixing. The strains were then aseptically inoculated into 120 ml of MRS broth in an Erlenmeyer flask of 250 ml and cultivated under aerobic conditions at 30° C. for three days without mixing. The strains were then inoculated into 0.6 l of MRS broth in an Erlenmeyer flask. The cultivation was continued under aerobic conditions at 30° C. for three days without mixing.

The resultant culture broth contained $1 \times 10^{10}$ to $1 \times 10^{11}$ CFU/l of lactic acid bacteria (colony-forming units/liter of culture broth).

The culture broth was diluted to a ratio of about 1:10 with water. These diluted culture broths were used as a test preparation in field sprayings.

EXAMPLE 2

Treating Growing Barley with Lactic Acid Bacteria

Finnish barley of a variety called "Kustaa" was cultivated in test squares of 10 m² (fields 701 to 704). There were three test squares for each test preparation. A culture broth prepared according to Example 1, containing *Lactobacillus plantarum* VTT-E-78076 and *Pediococcus pentosaceus* VTT-E-90390, was sprayed on growing barley immediately after the ear emergence, and a culture broth containing *Pediococcus pentosaceus* VTT-E-90390 was also sprayed ten days after the ear emergence. Each test preparation used for the spraying contained $1 \times 10^9$ to $1 \times 10^{10}$ CFU/l of lactic acid bacteria, and the preparation was used in the amount of 200 l/ha. The sprayings were performed with an Azo propane sprayer comprising an extension arm of 2 m with nozzles at intervals of 50 cm. The control field was not treated at all. The barley was threshed when it was ripe, and it was then dried. The kernels were stored in a cool and dry place until the malting. The test arrangement is shown in Table 1.

TABLE 1

Test arrangement of the lactic acid bacterial treatment of growing barley

| Field No. | Description |
|---|---|
| 701 | Control (untreated) |
| 702 | Treatznent with *L. plantarum* VTT-E-78076 preparation right after the ear emergence (200 l/ha) |
| 703 | Treatment with *P. pentosaceus* VTT-E-90390 preparation right after the ear emergence (200 l/ha) |
| 704 | Treatment with *P. pentosaceus* VTT-E-90390 preparation ten days after the ear emergence (200 l/ha) |

EXAMPLE 3

Effect of the Lactic Acid Bacterial Treatment on the Germinability of Barley

The effect of the lactic acid bacterial treatment of growing barley on the germinability of barley was estimated by determining the germinability of dry barley kernels, i.e. the germination capacity ($H_2O_2$) was determined in percentages, as well as the germination energy and water sensitivity after 3 and 5 days in percentages, utilizing methods known from malting, described for example in EBC-Analytica, 4th edition, Analysis Committee of EBC (ed.), Brauerei- und Getränke Rundschau, Zurich, 1987.

In short, in determining the germination capacity the kernels are germinated in a 0.75% hydrogen peroxide solution in order to end the dormancy of the barley. The germination capacity represents the number of living kernels. The germination energy which represents the germinability of the barley is determined by germinating the kernels in a Petri dish on a moistened absorbent paper. Water sensitivity is determined in the same way as the germination energy, but utilizing a larger amount of water.

The results are shown in Table 2, provided with the same abbreviations as Table 1.

TABLE 2

Effect of the lactic acid bacterial spraying on the germination of barley

| Percentage of kernals that have germinated | Field/preparation | | | |
|---|---|---|---|---|
| | 701 control | 702 | 703 | 704 |
| Germination capacity ($H_2O_2$) (%) | 98 | 98 | 99 | 99 |
| Germination energy 3/5 days (%) | 96/98 | 96/93 | 90/94 | 94/97 |
| Water sensitivity 3/5 days (%) | 26/36 | 28/35 | 42/51 | 35/47 |

Spraying a growing cereal in the field, at different stages of ear emergence, with lactic acid bacteria according to the invention has no essential effect on the germination capacity of barley kernels. In tests 702 and 703, the use of lactic acid bacteria slightly reduced the germination energy, but clearly reduced the water sensitivity of the kernels, especially in tests 703 and 704.

EXAMPLE 4

Effects of the Lactic Acid Bacterial Treatment on the Amounts of Microbes in the Barley The effects of the lactic acid bacterial treatment of growing barley on the microbial amounts of the barley kernels was analyzed by assaying Fusarium moulds, total count of bacteria, lactic acid bacteria and yeasts.

The proportion of kernels contaminated with Fusarium moulds was assayed on Czapek Iprodion Dicloral agar (CZID-agar, Difco) specific for Fusarium moulds, according to a method described by Abildgren et al. [Lett. Appl. Microbiol. 5 (1987) 83–86]. The Fusarium moulds were identified on the basis of the typical colony and spore morphology.

The total bacteria content was assayed on Plate Count agar (Difco), and the lactic acid bacteria were assayed on MRS agar (Oxoid) with methods conventional in microbiology. The yeasts were assayed on Saboraud agar (Oxoid). The results are shown in Table 3, provided with the same abbreviations as Table 1.

TABLE 3

Effect of the lactic acid bacterial spraying on the amounts of microbes in the barley

| Microbial assay | Field/preparation | | | |
|---|---|---|---|---|
| | 701 control | 702 | 703 | 704 |
| Fusarium moulds (% of contaminated kernals) | 57 | 43 | 66 | 46 |
| Bacterial total count CFU/g ds* | $4.7 \times 10^7$ | $3.5 \times 10^7$ | $3.8 \times 10^7$ | $4.1 \times 10^7$ |
| Lactic acid bacteria | $3.3 \times 10^1$ | $2.2 \times 10^2$ | $2.2 \times 10^2$ | $2.2 \times 10^2$ |

TABLE 3-continued

Effect of the lactic acid bacterial spraying on the amounts of microbes in the barley

| Microbial assay | Field/preparation | | | |
|---|---|---|---|---|
| | 701 control | 702 | 703 | 704 |
| CFU/g ds* Yeasts CFU/g ds* | $2.2 \times 10^3$ | $6.7 \times 10^3$ | $6.6 \times 10^3$ | $3.3 \times 10^3$ |

*colony-forming units/gram of dry substance

Treating a growing cereal with lactic acid bacteria according to the present invention slightly reduces the amount of kernels contaminated with Fusarium mould and the amount of total bacteria, except for test 703. The use of the lactic acid bacteria slightly increases the amount of yeast and lactic acid bacteria compared with the control.

EXAMPLE 5

Effect of the Lactic Acid Bacterial Treatment on the Quality and Yield of Barley The effect of the treatment according to the present invention on the yield and quality of the barley kernels was assayed according to the directions defined in a decision by the Finnish Ministry of Agriculture concerning the determination of cereal quality, issued in Helsinki, Jul. 1, 1991. The yield (kg/ha), the weight of a thousand kernels (g), and the weight of a hectoliter (kg) were determined by weighing. The falling number and protein content are known factors describing the quality of a cereal, and they were determined with methods generally used in the art. The results are shown in Table 4, provided with the same abbreviations as Table 1.

TABLE 4

Effect of the lactic acid bacterial spraying on the yield and quality of barley

| Assay | Field/preparation | | | |
|---|---|---|---|---|
| | 701 control | 702 | 703 | 704 |
| Yield (kg/ha) | 5670 | 5810 | 5540 | 5640 |
| Weight of a thousand kernals (g) | 44.8 | 45.0 | 44.6 | 44.5 |
| Weight of a hectoliter (kg) | 72.3 | 72.2 | 72.4 | 72.9 |
| Falling number (s) | 99 | 108 | 114 | 120 |
| Protein (%) | 11.4 | 11.2 | 11.6 | 11.5 |

Treating a growing cereal with lactic acid bacteria according to the invention had a clearly positive effect on the falling number for all preparations. The falling number increased most (20%) as a result of a treatment with *Pediococcus pentosaceus*. The treatment did not have an essential effect on the other parameters describing the yield and quality of barley as compared with the control.

EXAMPLE 6

Effect of the Lactic Acid Bacterial Treatment on the Amounts of Microbes in Barley Malt Barley treated according to the invention was used to produce malt, so that the effect of the lactic acid bacterial treatment on barley malt could be analyzed. Kernels originating in each barley culture and in the control culture were malted in batches of one kilogram in a test malting device (Seeger) with a standard method.

The malt prepared from the barley was assayed for total bacteria, lactic acid bacteria and yeasts in the manner described in Example 4. The results are shown in Table 5, provided with the same abbreviations as Example 1.

TABLE 5

Effect of the lactic acid bacterial treatment on the amounts of microbes in the malt

| | Field/preparation | | | |
|---|---|---|---|---|
| Microbial assay | 701 control | 702 | 703 | 704 |
| Bacterial total count[a] CFU/g ds[b] | $1.0 \times 10^8$ | $1.1 \times 10^8$ | $9.2 \times 10^7$ | $4.7 \times 10^7$ |
| Lactic acid bacteria[c] CFU/g ds[b] | $4.8 \times 10^6$ | $3.9 \times 10^6$ | $3.4 \times 10^6$ | $4.3 \times 10^6$ |
| Yeasts[d] CFU/g ds[b] | $1.3 \times 10^5$ | $5.0 \times 10^4$ | $5.4 \times 10^4$ | $7.3 \times 10^4$ |

[a]assay on Plate count agar (Difco)
[b]colony-forming units/gram of dry substance
[c]assay on MRS agar (Oxoid)
[d]assay on Saboraud agar (Oxoid)

Treating a growing cereal with lactic acid bacteria according to the invention did not have an essential effect on the amounts of microbes in malt prepared from the barley.

EXAMPLE 7

Effect of the Lactic Acid Bacterial Treatment on the Quality and Properties of the Malt The physico-chemical quality of the malt prepared according to Example 6 from barley treated in the field according to the invention was analyzed with methods known from malting, described in detail in EBC-Analytica, 4th edition, Analysis Committee of EBC (ed.), Brauerei- und Getränke Rundschau, Zurich, 1987. The quality of the malts was also examined from wort prepared through Büchner filtration with a modification of a method by Brown et al. (Proc. 3rd Aviemore Conf. Malt. Brew. Distill. Aviemore 1990, Institute of Brewing, 313–318), the modification being described by Sjöholm et al. [Monatsschrift fur Brauwissenschaft 5 (1994) 165–171].

TABLE 6

Effect of the lactic acid bacterial treatment on the analytic values of the malt

| | Field/preparation | | | |
|---|---|---|---|---|
| Malt analysis | 701 control | 702 | 703 | 704 |
| Moisture (%) | 4.2 | 4.1 | 4.1 | 4.1 |
| Extract from flour (%/ds) | 80.8 | 81.1 | 81.2 | 81.2 |
| Wort colour °EBC | 4.1 | 4.1 | 4.4 | 4.4 |
| pH of wort | 6.02 | 6.01 | 5.99 | 5.98 |
| Flour/coarse grain difference (%/ds) | 2.3 | 1.8 | 1.5 | 1.7 |
| Friability flour (%) | 80 | 81 | 83 | 81 |

TABLE 6-continued

Effect of the lactic acid bacterial treatment on the analytic values of the malt

| | Field/preparation | | | |
|---|---|---|---|---|
| Malt analysis | 701 control | 702 | 703 | 704 |
| Friability (%) (>2,2 mm) | 4.4 | 3.8 | 2.2 | 3.2 |
| Malt modification (%) (Calcofluor) | 89 | 94 | 93 | 89 |
| Homogeneity (%) (Calcofluor) | 69 | 77 | 66 | 68 |
| Viscosity of wort (mPas) | 1.48 | 1.49 | 1.48 | 1.48 |
| Filtration time flour/coarse grain (min) | 60/240 | 42/150 | 45/120 | 45/120 |
| β-glucan of wort (mg/l) | 222 | 189 | 184 | 194 |
| Soluble nitrogen (mg/100 g) | 812 | 822 | 820 | 826 |
| Protein (%/ds) | 11.5 | 11.4 | 11.5 | 11.1 |
| Degree of solubility of protein (Kolbach) (%) | 44 | 45 | 45 | 47 |
| FAN (mg/l) | 166 | 183 | 176 | 187 |
| Saccharification time (min) | <10 | <10 | <10 | <10 |
| α-amylase (DU/g ds) | 67 | 69 | 74 | 74 |
| Diast. power (WK/100 g ds) | 370 | 350 | 350 | 350 |

TABLE 7

Effect of the lactic acid bacterial treatment on the properties of the malt (Büchner filtration)

| | Field/preparation | | | |
|---|---|---|---|---|
| Property | 701 control | 702 | 703 | 704 |
| Extract content of wort (%) | 16.09 | 16.14 | 16.14 | 16.20 |
| Actual extract yield (%/ds) | 21.6 | 32.5 | 34.3 | 34.6 |
| pH of wort | 5.69 | 5.70 | 5.68 | 5.69 |

The results of Tables 6 and 7 show that the lactic acid bacterial treatment of growing barley according to the invention had the following advantageous effects on the quality of malt prepared from the barley: the extract content and yield, as well as FAN and α-amylase increased, according to several different analyses (malt modification %, flour/coarse grain difference, friability and the β-glucan content of the wort), the modification of the malt increased and the filterability of the wort became considerably faster. The most important of these is in practice the advantageous effect on the rate of filtration (see FIG. 1). The method according to the invention had no effect on the other values of malt analysis.

EXAMPLE 8

Effect of the Treatment on the Gushing Tendency of Beer

The effect of the lactic acid bacterial treatment of growing barley according to the invention on the gushing tendency of beer was determined with the Carlsberg rapid method in the manner described by Vaag et al. [Eur. Brew. Conv. Proc. 24th Congr., Oslo (1993) 155–1629].

Samples a to c were prepared in the following manner. Barley samples treated with lactic acid bacteria according to the invention were malted in the manner described in Example 6. 100 grams of each resultant malt sample were mixed with 400 ml of distilled water in a laboratory blender at maximum speed. The suspension was centrifuged at 5000 rpm, and the supernatant was concentrated by boiling to about half of its volume. The resultant precipitate was removed through filtration. The filtrate was cooled, and the volume was adjusted to 200 ml with distilled water. 50 ml of beer were removed from three beer bottles cooled to a low temperature (4°–10° C.) and replaced with 50 ml of malt extract. The bottles were carefully shaken in order to replace the air in the neck of the bottle with foam, and the bottles were then corked and pasteurized for 20 minutes at 60° C. After the cooling the bottles were rocked in a horizontal position for three days before they were tested in order to induce gushing.

The bottles were weighed and left undisturbed for ten minutes. They were then turned upside down three times, left undisturbed for 30 seconds and finally opened. If gushing occurred, the bottles were weighed again, and the amount of beer that had escaped from the bottles was calculated. Gushing Malt A, which contains *Fusarium poae* mould (Carlsberg, Copenhagen, Denmark) was used as the standard for gushing.

The results are shown in Table 8, provided with the same abbreviations as Example 1.

TABLE 8

Effect of the lactic acid bacterial treatment on the gushing tendency of beer

| | Amount of gushing (g) Field | | | |
|---|---|---|---|---|
| | 701 control | 702 | 703 | 704 |
| Sample a | 43.1 | 14.0 | 31.0 | 0.1 |
| Sample b | 55.0 | 0.1 | 24.0 | 23.1 |
| Sample c | 38.9 | 14.7 | 11.9 | 21.6 |
| Average | 45.7 | 9.8 | 22.3 | 14.9 |
| Gushing standard | 54.2 | | | |

The gushing tendency of all malts prepared from barley treated with lactic acid bacteria according to the invention had substantially decreased. It decreased most in malt prepared from barley (702) sprayed in the field with a culture broth containing *Lactobacillus plantarum* VTT-E-78076: the gushing tendency decreased to almost one fifth as compared with malt prepared from untreated barley, and to almost one sixth as compared with the gushing standard. The gushing values obtained with malt prepared from barley sprayed in the field with a culture broth containing *Pediococcus pentosaceus* VTT-E-90390 (703) right after the ear emergence, or ten days later, decreased 51% and 67% respectively, as compared with the control, and 59% and 73% respectively, as compared with the gushing standard.

I claim:

1. A method for treating cereals in order to improve the malting or baking properties, falling number, or microbial flora of seeds, comprising treating the cereal in the field or under field conditions when the seeds develop, by spraying the cereal with a lactic acid bacterial preparation.

2. A method according to claim 1, wherein the treating step is performed during ear emergence.

3. A method according to claim 2, wherein the cereal is barley suitable for malting.

4. A method according to claim 1, wherein the treating step comprises treating the cereal with a lactic acid bacterium belonging to Lactobacillus or Pediococcus, or a mixture thereof.

5. A method according to claim 4, wherein the lactic acid bacterial preparation comprises *Lactobacillus plantarum* or *Pediococcus pentosaceus*.

6. A method for using lactic acid bacteria, comprising treating a plant in the field or under field conditions while its seeds develop, with a preparation including lactic acid bacteria.

7. A method according to claim 6, wherein the plant comprises a cereal suitable for malting or milling.

8. A plant product comprising a plant treated with lactic acid bacteria in the field or under field conditions while its seeds develop.

9. A method for inhibiting the growth of mold in seeds of a harvested plant, comprising treating the plant during its seed development phase with lactic acid bacteria.

10. A method according to claim 9, wherein the mold comprises Fusarium species.

* * * * *